(12) United States Patent
Jhaveri et al.

(10) Patent No.: US 7,932,096 B2
(45) Date of Patent: Apr. 26, 2011

(54) TRIOXYETHYLENE GOLD NANOCLUSTERS FUNCTIONALIZED WITH A SINGLE DNA

(75) Inventors: Sulay Jhaveri, Alexandria, VA (US); Mario Ancona, Alexandria, VA (US); Edward E Foos, Alexandria, VA (US); Eddie L Chang, Silver Spring, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 12/574,401

(22) Filed: Oct. 6, 2009

(65) Prior Publication Data

US 2010/0029921 A1 Feb. 4, 2010

Related U.S. Application Data

(60) Division of application No. 11/278,502, filed on Apr. 3, 2006, now Pat. No. 7,655,474, which is a continuation-in-part of application No. 10/206,431, filed on Jul. 29, 2002, now Pat. No. 7,404,928.

(60) Provisional application No. 60/668,876, filed on Apr. 1, 2005.

(51) Int. Cl.
*G01N 21/75* (2006.01)
(52) U.S. Cl. ........ 436/166; 436/151; 436/183; 436/524; 436/525; 422/82.01; 422/82.02; 422/82.03
(58) Field of Classification Search .................... None
See application file for complete search history.

(56) References Cited

U.S. PATENT DOCUMENTS

2005/0074551 A1* 4/2005 Huang et al. .................. 427/212

FOREIGN PATENT DOCUMENTS

WO WO 98/59362 * 12/1998

OTHER PUBLICATIONS

Durrant, Ian. et al. Nonradioactive oligonucleotide probe labeling, 1994, Protocols for Gene Analysis, vol. 31, pp. 163-175.*
Mirkin et al, A DNA-based method for rationally assembling nanoparticles into macroscopic materials, Nature, vol. 382, p. 607-609 (Aug. 15, 1996).

(Continued)

*Primary Examiner* — Vickie Kim
*Assistant Examiner* — Robert Xu
(74) *Attorney, Agent, or Firm* — Amy Ressing; Roy Roberts

(57) ABSTRACT

A method of making a nanoclusters functionalized with a single DNA strand comprising the steps of providing nanoclusters, combining said nanoclusters with thiolated DNA, incubating said nanoclusters and thiolated DNA mixture, combining said mixture with a solution comprising ethanol and dichloromethane; separating said mixture into an aqueous phase and an organic phase, mixing said aqueous phase with a solution comprising dicholormethane and NaCl, and separating the mixture into an aqueous phase and an organic phase; wherein said organic phase comprises said nanoclusters functionalized with a single DNA strand. Further, provided is a nanocluster functionalized with a single DNA strand comprising a nanocluster, said nanocluster being functionalized with a single DNA strand, said DNA strand having a length of about 10 to about 50 bases.

13 Claims, 5 Drawing Sheets

OTHER PUBLICATIONS

Alivisatos, et al, Organization of 'nanocrystal molecules' using DNA, Nature, vol. 382, p. 609-611 (Aug. 15, 1996).

Snow et al, Size-Induced Metal to Semiconductor Transition in a Stabilized Gold Cluster Ensemble, Chemistry of Material, vol. 10, No. 4, p. 947-949, (Mar. 12, 1998).

Hostetler, et al, Alkanethiolate Gold Cluster Molecules with Core Diameters from 1.5 to 5.2 nm: Core and Monolayer Properties as a Function of Core Size, Langmuir, vol. 14, p. 17-30, (Jan. 6, 1998).

* cited by examiner

TRIOXYETHYLENE GOLD NANOCLUSTERS FUNCTIONALIZED WITH A SINGLE DNA

CROSS-REFERENCE TO RELATED APPLICATIONS

This Application is a Divisional of U.S. patent application Ser. No. 11/278,502, which was a Continuation-in-Part of U.S. application Ser. No. 10/206,431, now issued as U.S. Pat. No. 7,404,928, filed Jul. 21, 2002 and a Non-Prov of Prov (35 USC 119(e)) application 60/668,876 filed on Apr. 1, 2005, the entirety of each is incorporated herein by reference.

BACKGROUND OF THE INVENTION

Gold nanoclusters (GNCs) have received been considered as potential building blocks for a variety of nanoscale applications, including chemical sensing, electronics, optics, and biology. A scalable method for isolating significant quantities of GNCs with a known number of DNA strands per GNC would be useful in nanoscale applications dependent on using DNA molecular recognition in patterned self-assembly scemes, as DNA, with its highly specific base-pairing is attractive as the basis of self-assembly of nanoclusters. Earlier work demonstrated the feasibility of this approach using GNCs coupled with multiple oligonucleotides; but to go beyond these assemblies, and for diagnostics based on the quantification of hybridization events, it is essential to work with GNCs bearing one and only one oligonucleotide strand. Methods for creating singly-attached nanoclusters have been developed, see Mirkin, et al, *J. Nature* 1996, 382, 607-609 and Alivisatos, et al, *Nature* 1996, 382, 609-611. However, the methods of Alivaisatos and Mirkin used gold nanoclusters that were stabilized by citrate, by phosphine or by thiolated DNA, which are charged, which can lead to nonspecific interactions, either attractive or repulsive, particularly at low ionic strength. Additionally, these methods are appear to be limited to ssDNA tags of at least 50 bases long, which could create an imprecision in the ability to position small clusters by a templating strategy.

Therefore, there is a need in the art for a method for creating singly-attached nanoclusters that are not stabilized by citrate, phosphine or by thiolated DNAs. Additionally, there is a need in the art for a method for creating singly-attached nanoclusters are less than 50 bases long, allowing for the ability to position the cluster via a templating strategy.

These and other objectives are achieved by a method that utilizes a neutral cluster and allow for the synthesis and isolation of singly-attached clusters with ssDNA as short as 10-15 bases.

BRIEF SUMMARY OF THE INVENTION

These and other objects are provided by a method of making a nanoclusters functionalized with a single DNA strand comprising the steps of providing nanoclusters, combining said nanoclusters with thiolated DNA, incubating said nanoclusters and thiolated DNA mixture, combining said mixture with a solution comprising ethanol and dichloromethane; separating said mixture into an aqueous phase and an organic phase, mixing said aqueous phase with a solution comprising dicholormethane and NaCl, and separating the mixture into an aqueous phase and an organic phase; wherein said organic phase comprises said nanoclusters functionalized with a single DNA strand. Further, provided is a nanocluster functionalized with a single DNA strand comprising a nanocluster, said nanocluster being functionalized with a single DNA strand, said DNA strand having a length of about 10 to about 50 bases.

The method of the present invention works with oligonucleotides as short as about 10 to about 15 bases long. The method works with highly stable and charge neutral triethylene oxide-coated clusters, yielding product suitable for quantitative detection of hybridization events, for bio-molecular-directed self assembly of nanoparticles and use in future Coulomb blockade-based electronic devices. The method does not rely on the gel electrophoresis technique, which is cumbersome and low-throughput for isolation uses. The method is readily scaled up to isolate large quantities of product. The method works with nanoclusters ranging in size from about 1 to about 10 nm.

DETAILED DESCRIPTION OF THE INVENTION

Figure 1A:
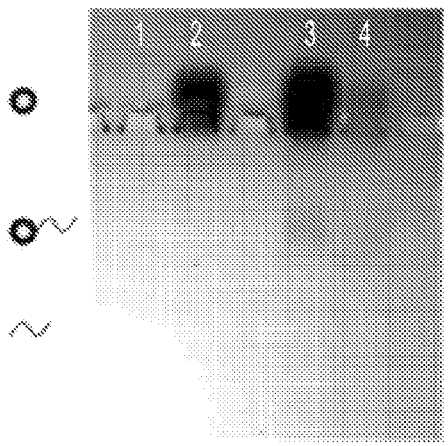
FIG. 1 show gel electrophoresis results that compare the products obtained with AuEO3/DNA ratios of 1:1 and 11:1.

A method of synthesizing and isolating nanoclusters functionalized with a single ssDNA strand is described. The clusters can be comprised of metal or semiconductor material. Preferably, the clusters are comprised of Au, Ag, or CdSe. The clusters range in size from about 1 to about 10 nm. Additionally, the clusters can be coated with a monolayer of trioxyethylene-thiol molecules. The ssDNA length ranges from about 10 to about 50 bases, or about 3.4 to about 17 nm in length. Preferably, for templating purposes, the diameter of the cluster is comparable to the length of the ssDNA. Characterization by UV-vis absorbance spectroscopy demonstrates that the product isolated by this technique has a DNA/GNC ratio approaching 1:1.

Initial work on the preparation of DNA-GNC conjugates employed citrate-stabilized gold colloids that were subsequently passivated with a monolayer of anionic phosphine molecules in order to avoid nonspecific binding of nucleic acids and overcome the tendency toward self-agglomerization and precipitation. Another type of GNC, denoted as AuEO3 which consists of a 1.8±0.2 nm gold core encapsulated by a monolayer of a methyl-terminated tri(oxyethylene) thiol, $CH_3(OCH_2CH_2)_3SH$, can be useful in the present invention. See related case U.S. Pat. No. 7,404,928, the entirely of which is incorporated herein by reference. Being direct analogues of the well-known alkanethiol monolayer protected clusters, AuEO3 are very attractive for use in combination with biomolecules in that their synthesis exploits the well-understood Au-thiol chemistry yet these GNCs are water-soluble, charge-neutral, and show stability over a broad range of pH and ionic strengths. Charge neutrality is a particularly important attribute for cluster/biomolecule coupling since a ligand shell that contains ionic species or which is able to participate in hydrogen bonding may lead to self-agglomerization or nonspecific interactions with the DNA. The trioxyethylene shells are expected to suppress such unwanted processes much like similar polyethylene coatings on flat gold surfaces. These AuEO3 clusters resist the nonspecific binding of both proteins and nucleic acids. Finally, from an electrical perspective these clusters are attractive because (i) they are small enough (<3 nm) to show Coulomb blockade effects at room temperature, and (ii) their trioxyethylene coating is not so thick as to block all electron transport between neighboring clusters. U.S. application Ser. No. 10/206,431, now issued as U.S. Pat. No. 7,404,928, discloses a thiol terminated ethylene oxide oligomer having the formula CH3 (OCH2CH2)xSH, wherein the value of x varies from one to ten, and is ideally two, three or four. The thiol terminated ethylene oxide oligomer is formed and then substituted onto a gold nanocluster surface using a thiol-exchange reaction to form a charge-neutral, non-ionizable, water soluble, ethylene oxide protected gold nanocluster. The gold nanoclusters made using the thiol terminated ethylene oxide oligomer are easily prepared, small in core size, stable, water-soluble, charge-neutral, and able to undergo thiol-exchange reactions. These gold nanoclusters have important implications for sensors and for nanostructure fabrication in aqueous environments, e.g., in DNA-based assembly.

The existing method for isolating conjugates containing both singly and multiply functionalized clusters from unreacted starting materials is via gel electrophoresis, followed by elution of the appropriate band. This is a tedious procedure that is not readily scaled up to larger volumes. Furthermore, it appears to be ineffective when the DNA lengths fall below about 50 bases. This latter consideration is important because in order for a ssDNA to serve as a proper "address label" for a GNC, the length of the DNA is preferably comparable to the cluster size. This implies ssDNAs on the order of 15 bases long. The DNA oligomer (5'HO-(CH2)6-S-S-(CH2)6-ACA-CACACACACACA-fluorescein-3' (SEQ. ID. NO.: 1)) was synthesized and HPLC purified (Integrated DNA Technologies). The disulfide on the 5'-terminus was first reduced with a freshly prepared 75 mM dithiothreitol (Pierce) solution, and the resulting monothiolated oligo was purified on a 15% acrylamide gel (Bio-Rad). The oligo from the excised gel slices was eluted into 1 mL distilled, deionized water, (R=18 MΩcm-1). The concentration of the DNA was determined by measuring A260 using a molar extinction coefficient of 172, 000 L mol-1 cm-1 (provided by the manufacturer). The new protocol that stoichiometrically favors the formation of singly functionalized GNCs, which are then purified by exploiting solubility differences.

Figure 1B:
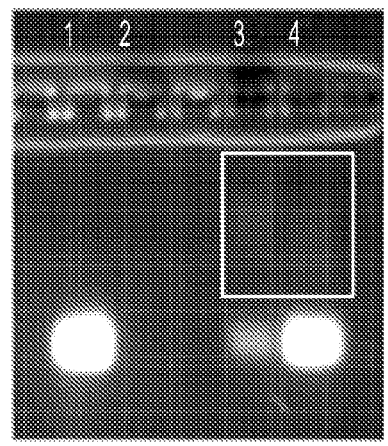
Figure 1C:
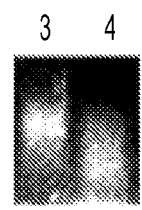

This is a relatively slow reaction requiring several hours of incubation. To ensure that almost no multifunctionalized clusters are formed, an excess of clusters is used. FIG. 1 shows gel electrophoresis images that compare the products obtained with AuEO3/DNA ratios of 1:1 (reaction 1) and 11:1 (reaction 2), as seen in luminescence mode (FIG. 1A) showing the reddish brown of the AuEO3 and through a fluorescence filter (FIG. 1B) that highlights the fluorescein labeled DNA. Lanes 3 (11:1) and 4 (1:1) show the products as running distinctly from the unreacted DNA (lane 1) and the unreacted AuEO3 (lane 2). Furthermore, while the product in lane 3 appears to be mostly a single band, the product in lane 4 yields a more diffuse band with a higher average mobility under the fluorescent filter, consistent with a scenario in which cluster products with both single and multiple DNAs attached are present in the mixture.

Agarose gels, 2%, were made in TBE (Tris-borate-EDTA buffer, Sigma) and run in 0.5× TBE on a horizontal gel electrophoresis apparatus. All samples were treated with 0.2 vol of 30% glycerol prior to loading. The samples were run on the gel under an applied potential of 100 V for 20 min or until the fluorescent DNA ran past the middle of the gel. The gels were viewed using a Kodak Image Station 440 digital camera.

Additional short ssDNAs attached to AuEO3 will increase the electrophoretic mobility of the DNA$_{(n)}$-AuEO3 conjugate by increasing the negative charge density without appreciably adding to its hydrodynamic radius. The extent to which the additional DNA strands, which add both size and charge, affect the electrophoretic mobility of conjugates is currently under investigation. The existence of these bands suggests that the electrophoretic separation of DNA-GNC conjugates may also be limited by the ratio of the cluster size to DNA length and/or by cluster charge and that the limit of 50 bases cited previously was merely a constraint associated with a different system and does not apply here.

Figure 2A:
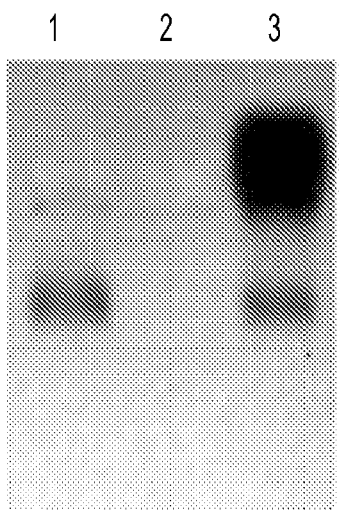
FIG. 2 shows gel electrophoresis results showing isolation of AuEO3 nanoclusters Functionalized with a single DNA.
Figure 2B:
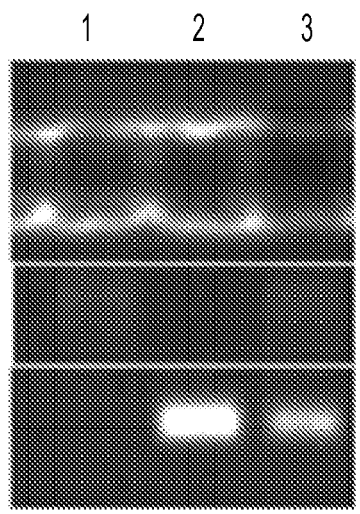
Figure 2C:
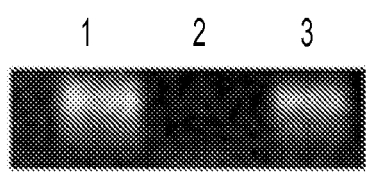

Electrophoretic harvesting of product is both tedious and yields very little product. The unique solubility properties of the trioxyethylene clusters enables scaling up; it is very likely that this technique is specific for AuEO3 and would not work with the citrate clusters and their derivatives used by others. AuEO3, although water-soluble, preferentially partitions into the organic phase in a binary solvent system of water and $CH_2Cl_2$, whereas DNA prefers the aqueous phase. Furthermore, we find that ethanol, which is miscible in both $CH_2Cl_2$ and $H_2O$, facilitates the migration of the components to their preferred phases. When the AuEO3-DNA reaction mixture (in $H_2O$) is added to a 1:2 mixture of ethanol in dichloromethane, a large fraction of the unreacted AuEO3 is found to migrate into the ethanol/$CH_2Cl_2$ phase, whereas the GNC-DNA conjugates and the unreacted DNA are retained in the ethanol/water phase. The DNA-AuEO3 reaction (300 μL) was mixed with 300 μL of ethanol and 600 μL of $CH_2Cl_2$. The tube was vigorously shaken and then spun on a benchtop centrifuge for 10 s to separate the two phases. The top phase, along with the opaque film between the phases, was transferred to a fresh tube. To this mostly aqueous phase, 300 μL of ethanol and 600 μL of $CH_2Cl_2$ were added, and the aqueous phase was isolated again. This was repeated three more times, and the volume of the aqueous phase diminished with every step due to incremental amounts of water becoming more and more miscible in the ethanolic organic phase. At this point, the aqueous phase bore a dark reddish-brown color indicative of AuEO3, and the organic phase bore no color. A final transfer of the aqueous phase into a fresh tube containing the ethanol/dichloromethane mixture resulted in total immersion and an apparent loss of phase separation. The five collected organic phases were subsequently rinsed with the same aliquot of 200 μL DIW to recover DNA that may have partitioned in the organic phase. The aqueous phase from the collected washes contained free DNA and AuEO3 attached to DNA. To this sample, 50 μL of a 4 M NaCl solution, buffered with 20 mM sodium phosphate, pH 7, and 200 μL of $CH_2Cl_2$ were added. The tube was shaken and spun to separate the phases as before, and the AuEO3 modified with DNA was extracted into the organic phase. The organic phase was subsequently washed with an additional 200 μL of a 1 M NaCl solution, buffered with 5 mM sodium phosphate, pH 7. The $CH_2Cl_2$ showed a light reddish-brown color, and when viewed under a fluorescent light, the salt-containing aqueous phase indicated the presence of the fluorescein-labeled DNA. Apparently, when the AuEO3 cluster is functionalized with DNA its solubility is sufficiently influenced by the presence of the charged species such that it resists transfer to the organic phase. This process is repeated several times, and the final separation of the cluster-DNA conjugate from free DNA is achieved by salting out the conjugates into $CH_2Cl_2$. The solvent is then evaporated and the product resuspended in water. This final product, isolated by extraction from 300 μL of reaction 2, is shown as Lane 1 in FIG. 2. Only a single product band is seen (with no free clusters or free DNA), confirming that the extraction procedure has succeeded.

Figure 3:
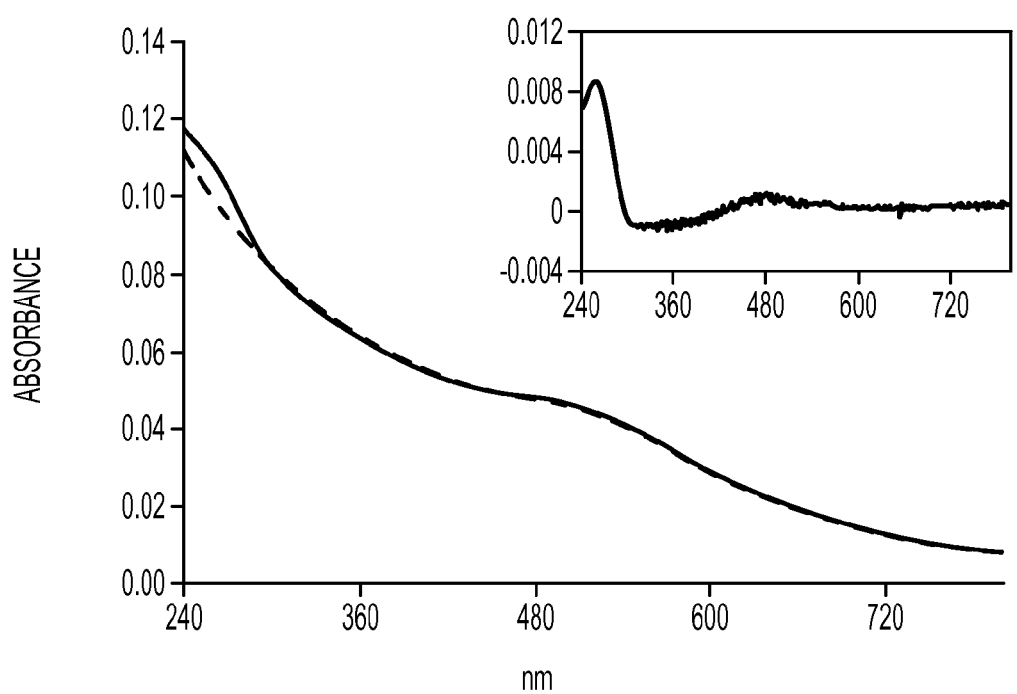
FIG. 3 shows UV-vis spectra of solutions of AuEO3 and AuEO3-DNA isolated by extraction.

Previous methods for assessing the degree of DNA conjugation to GNCs make use of fluorescence measurements that depend on hybridization with fluorescent complementary strands or that compare relative intensities of free fluorescent DNA in the presence or absence of nanoparticles when visualized on a gel. Both of these methods are indirect and have questions associated with the degree of hybridization and quenching. UV-vis measurements of AuEO3 and its DNA conjugate. Such a simple spectroscopic comparison is unique to AuEO3 and would not be possible with citrate- or phosphine-stabilized GNCs; the EO3SH is essentially transparent at 260 nm ($\in$=1600 L mol$^{-1}$ cm$^{-1}$, compared to $\in$=10,000 L mol$^{-1}$ cm$^{-1}$ for triphenylphosphine) and thus allows us to consider the absorbance of the conjugate as the sum of the absorbances of the DNA and the AuEO3 in this critical region where DNA has its signature peak. FIG. 3 shows UV-vis spectra for 40 μL of the DNA-AuEO3 and for a solution of unconjugated AuEO3 to be used as a baseline. The difference spectrum is shown in the inset in FIG. 3. FIG. 3 shows UV-vis spectra of solutions of (a) AuEO3 (- - -) and (b) AuEO3-DNA isolated by extraction (–). FIG. 3 inset shows background subtracted spectrum (b–a) used for quantifying DNA. Two peaks are visible in the difference spectrum, the first being the signature DNA peak at 260 nm and the second at 494 nm being associated with the DNA's fluorescein tag. A trace of a peak is also visible near 530 nm that is believed to be due to a slight increase in the surface plasmon absorbance of the cluster upon addition of the DNA. Such a change is not surprising given the sensitivity of plasmon absorption to the dielectric constant of the medium surrounding the gold nanocluster core. Based on the difference spectrum, we estimate the concentration of the DNA to be 56 nM. The concentration of AuEO3 based on $A_{507}$ is estimated to be 75 nM, indicating that on average 75% of the AuEO3 was labeled with DNA for this sample. This measurement was repeated four additional times with conjugates isolated from separate reactions and differing in initial concentrations of DNA, while still maintaining a ratio of AuEO3 to DNA greater than 10. While the concentration of attached DNA determined from the background subtracted spectrum in those isolated products ranged from 121 nM to 48 nM, the number of DNAs per GNC, averaged from all five samples measured, was 0.82±0.13. For three separate reactions in which the initial amount of the limiting reagent, the DNA, in the reaction was 480 pmol, the amount of product recovered, in terms of DNA, was 131±11 pmol, leading to a percent yield for the entire process of 27%. This number is a reflection on both the reaction efficiency itself as well as the efficiency of the extraction process, since a significant fraction (30%) of the DNA remains unattached even in the presence of an 11-fold excess of AuEO3, as seen in lane 3 of FIG. 2.

As a check on whether the plasmon absorbance of AuEO3 is changed in the presence of DNA, a control experiment was performed in which a single sample of AuEO3 was split into two fractions. Both fractions were incubated for 16 h at 35° C., one sample containing equimolar thiolated DNA while the other was diluted to an identical concentration with $H_2O$. It should be noted that the first fraction is essentially identical to the sample in lane 4 in FIG. 1 and thus most of its DNA is uncoupled to clusters. The UV-vis spectra for the two fractions were similar to those in FIG. 3, except that the peak at 494 nm associated with fluorescein was more pronounced. There was no observed change in the absorbance of AuEO3 due to the presence of DNA, and the ratio of DNA/AuEO3 for the sample with DNA was calculated to be very close to the expected value of 1 (0.95).

The measured molar ratio of DNA molecules to gold clusters in the isolated conjugates, although very close to unity as expected for $DNA_{(1)}$-AuEO3, was slightly lower at 0.82±0.13. The gel in FIG. 2 (lane 1) shows no evidence of either free DNA or free gold clusters indicates that, to within the resolution of the gel, all of the DNA was attached to clusters. The expected ratio of at least one, and perhaps greater if a small amount of $DNA_{(2)}$-AuEO3 had remained in the isolate. That this is not seen suggests that the discrepancy is instead associated with an effect of the coupling of the DNA to the cluster on the UV-vis absorbance. In particular, it could be that there is a moderate broadening and consequent height reduction of the 260 nm DNA absorption peak due to its attachment to the gold cluster, or perhaps an overall reduction in the 260 nm extinction coefficient of the attached DNA relative to that for free DNA in solution. Such reductions are known to occur with other adsorbents (mostly dyes), especially when the interaction with the gold surface is strong.

Example

A 15-mer DNA oligomer (5'HO-(CH2)6-S-S-(CH2)6-ACACACACACACACA-Fluorecein-3' (SEQ. ID. NO.: 1)) was synthesized and HPLC purified. The disulfide of the 5'-terminus was first reduced with a freshly prepared 75 mM dithiothreitol solution and the resulting mono-thiolated oligonucleotide was purified on a 15% acrylamide gel. The oligonucleotide from the excised gel slices was eluted into 1 mL distilled, deionized water, (R=18 M·Ω·cm-1). The concentration of the DNA was determined by measuring A260 using a molar extinction coefficient provided by the manufacturer. Prior to DNA-conjugation, the solution of AuEO3 was subjected to further purification on a P-6 size exclusion column to remove any residual EO3SH or AuEO3 with residual alkane thiol (which were insoluble in water). The concentration of the AuEO3 solution was estimated using a molar extinction coefficient of 5×105 L·mol-1·cm-1. This value was obtained by measuring an extinction coefficient at 512 nm of 9.7 L·g-1·cm-1 for a CHCl3 solution of the clusters, coupled with a molecular weight estimate of 52000 g·mol-1. The molecular weight estimate is based on the average core size of the nanoclusters as determined by TGA, using a previously published model of gold core atomic packing ad thiol ligand surface coverage.

Figure 5:
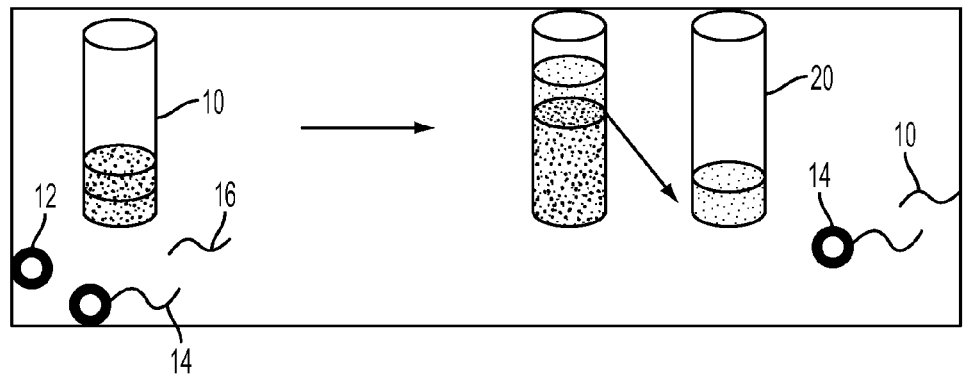
FIG. 5 shows the separation process.

A typical conjugation reaction starts with a mixture of 300 μL mixtures of 2 μM DNA and of 20 μM AuEO3 at 25° C. for at least approximately 16 hours. The DNA-AuE03 reaction volume (300 μL) was then added to a solution of 300 μL of ethanol and 600 μL of $CH_2Cl_2$. The mixture was vigorously shaken and spun down on a benchtop centrifuge for about 10 seconds to separate the two phases. The top aqueous phase, along with the opaque film in between the two phases was transferred to a fresh tube. To this mostly aqueous phase, 300 μL of ethanol and 600 μL of $CH_2Cl_2$ were further added and the aqueous phase was isolated again. The extraction was repeated 3 more times, with the volume of the aqueous phase decreasing at each step due to incremental amounts of water becoming more and more miscible in the ethanolic organic phase. At this point, the aqueous phase should have a dark reddish-brown color, indicating the presence of AuEO3, while the organic phase is colorless. FIG. 5 shows the separation process, where the initial phase (10) contains AuEO3 (12), DNA-AuEO3 (14), and free DNA (16). The extracted aqueous phase (20) contains the DNA-AuEO3 (14) and free DNA (16).

Figure 6:
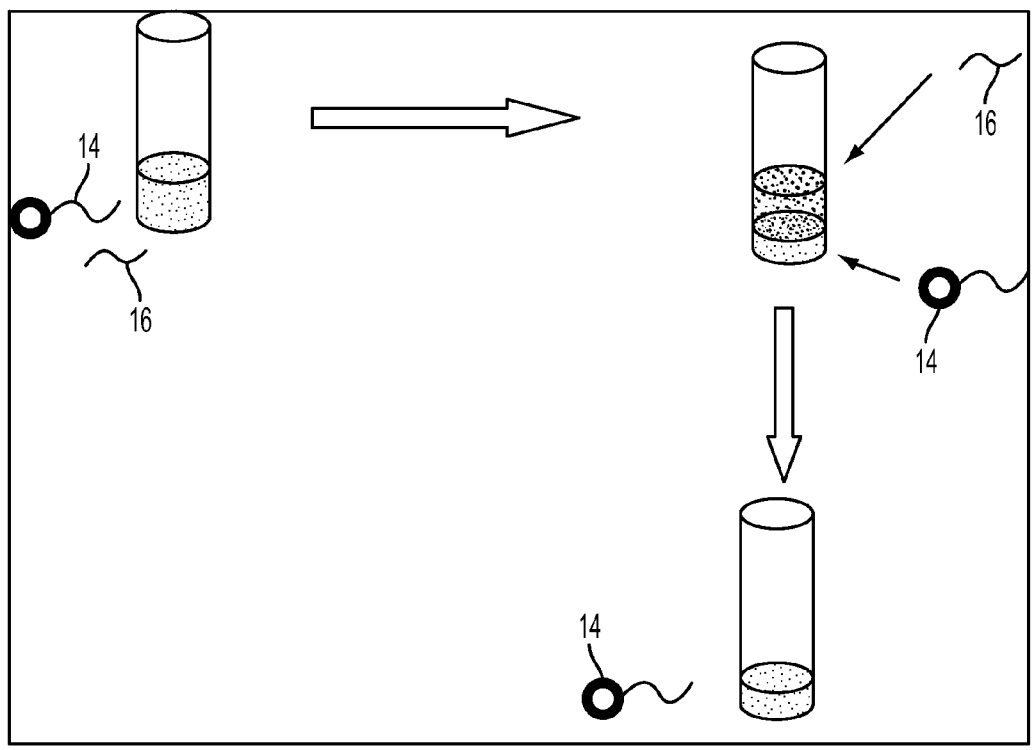
FIG. 6 shows the final water/$CH_2Cl_2$ wash.

The upper aqueous phase is added to 300 μL of $CH_2Cl_2$ and 500 μL of a 4 M NaCl solution, buffered with 20 mM sodium phosphate, pH 7. The mixture was shaken and spun to separate the phases as before. Any AuEO3 modified with DNA will be partitioned into the organic phase while the aqueous phase contains free DNA. The organic phase is finally washed with an additional 200 μL of a 1 M NaCl solution, buffered with a 5 mM sodium phosphate, pH 7. FIG. 6 shows the final water/$CH_2Cl_2$ wash, where DNA-AuEO3(14) is separated from free DNA (16).

Figure 4A:
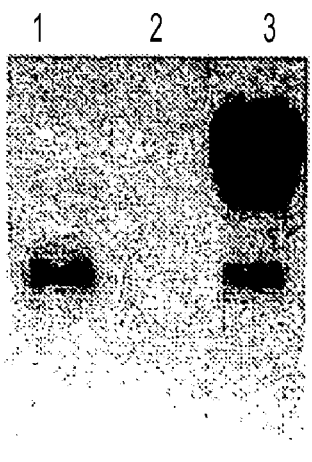
FIG. 4 shows the results of gel electrophoresis showing isolation of product viewed under luminescence and fluorescence mode.
Figure 4B:
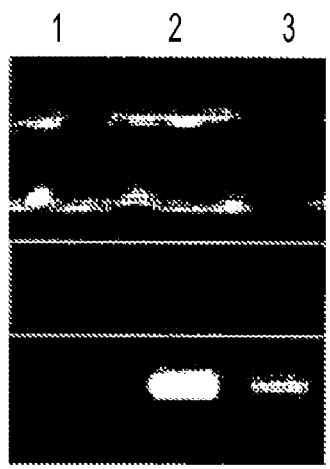
Figure 4C:

The $CH_2Cl_2$ organic phase, with the DNA-modified gold particles, exhibits a light, reddish brown color. The described procedure works equally well with fluorescent or non-fluorescent DNA. The isolated products may be characterized by gel electrophoresis and by UV and visible spectroscopy. FIG. 4 shows the results of gel electrophoresis showing isolation of product viewed under luminescence and fluorescence mode. FIG. 4A shows the luminescence mode, where lane 1 is the DNA-AuEO3 product, lane 2 is 11 pmol DNA, and lane 3 is 12 μL of reaction of 1.8 μM DNA and 20 μLM AuEO3, unextracted. FIG. 4B shows the fluorescence mode, where lane 1 is the DNA-AuEO3 product, lane 2 is the free DNA, and lane 3 is the unextracted reaction. FIG. 4C is viewed at higher sensitivity, showing product bands from lane 1 (the DNA-AuEO3 product) and lane 3, the unextracted reaction mixture.

Quantification of DNA concentration and that of the AuEO3 enables the calculation of a ration of DNA to AuEO3. The method of the present invention yields about 0.9-/-0.09 for the ratio of DNA to AuEO3. Overall yield using this method is about 27%.

The above description is that of a preferred embodiment of the invention. Various modifications and variations are possible in light of the above teachings. It is therefore to be understood that, within the scope of the appended claims, the invention may be practiced otherwise than as specifically described. Any reference to claim elements in the singular, e.g. using the articles "a," "an," "the," or "said" is not construed as limiting the element to the singular.

What is claimed as new and desired to be protected by Letters Patent of the United States is:

1. A purified nanocluster functionalized with a single DNA strand comprising: a purified nanocluster, wherein said nanocluster is coated with a monolayer of trioxyethylene-thiol molecules, said nanocluster being functionalized with a single mono-thiol-modified DNA strand, said mono-thiol-modified DNA strand having a length from about 10 bases to about 50 bases,
   wherein the purified nanocluster functionalized with a single DNA strand is obtained by combining the single mono-thiol-modified DNA strand with the nanocluster coated with the monolayer of trioxyethylene-thiol molecules to form a mixture;
combining said mixture with a binary solvent system comprising an aqueous phase and an organic phase; and separating the aqueous phase and the organic phase, wherein the organic phase comprises said at least one nanocluster functionalized with a single DNA strand.

2. The purified functionalized nanocluster of claim 1, wherein said nanocluster is comprised of metal or semiconductor material.

3. The purified functionalized nanocluster of claim 1, wherein said nanoclusters comprise Au, Ag or CdSe.

4. The purified functionalized nanocluster of claim 1, wherein said nanoclusters are AuEO3.

5. The purified functionalized nanocluster of claim 1, wherein said nanoclusters range in size from about 1 nm to about 10 nm.

6. The purified functionalized nanocluster of claim 1, wherein said nanocluster has a diameter that is comparable to the length of said mono-thiol-modified DNA strand.

7. A purified triethylene oxide-coated gold nanocluster functionalized with a single mono-thiol-modified DNA strand comprising: a triethylene oxide-coated gold nanocluster, said purified nanocluster being functionalized with a single mono-thiol-modified DNA strand, said DNA strand having a length of about 10 to about 50 bases,
   wherein the purified nanocluster functionalized with a single DNA strand is obtained by combining the single mono-thiol-modified DNA strand with the nanocluster coated with the monolayer of trioxyethylene-thiol molecules to form a mixture; combining said mixture with a binary solvent system comprising an aqueous phase and an organic phase; and separating the aqueous phase and

SEQUENCE LISTING

```
<160> NUMBER OF SEQ ID NOS: 1

<210> SEQ ID NO 1
<211> LENGTH: 15
<212> TYPE: DNA
<213> ORGANISM: Artificial
<220> FEATURE:
<223> OTHER INFORMATION: Artificial Sequence - synthesized
<220> FEATURE:
<221> NAME/KEY: misc_feature
<223> OTHER INFORMATION: 5'HO-(CH2)6-S-S-(CH2)6-ACACACACACACACA-
      Fluorecein-3'

<400> SEQUENCE: 1
acacacacac acaca                                                  15
``` the organic phase, wherein the organic phase comprises said at least one nanocluster functionalized with a single DNA strand.

8. The purified functionalized nanocluster of claim 7, wherein said nanoclusters range in size from about 1 nm to about 10 nm.

9. The functionalized purified nanocluster of claim 7, wherein said nanocluster has a diameter that is approximately comparable to the length of said mono-thiol-modified DNA strand.

10. A population of nanoclusters, the population comprising:
   at least 131 pmol of nanoclusters coated with monolayers of trioxythylene-thiol molecules and functionalized with mono-thiol-modified DNA strands having lengths from 10 bases to about 50 bases,
   wherein the population of nanoclusters has a molar ratio of DNA molecules to nanoclusters of between about unity and about 0.82,
   wherein the purified nanocluster functionalized with a single DNA strand is obtained by combining the single mono-thiol-modified DNA strand with the nanocluster coated with the monolayer of trioxyethylene-thiol molecules to form a mixture; combining said mixture with a binary solvent system comprising an aqueous phase and an organic phase; and separating the aqueous phase and the organic phase, wherein the organic phase comprises said at least one nanocluster functionalized with a single DNA strand.

11. The population of claim 10, wherein said nanoclusters comprise Au, Ag, or CdSe.

12. The population of claim 10, wherein said nanoclusters range in size from about 1 nm to about 10 nm.

13. The population of claim 10, wherein said population comprises almost no multifunctionalized nanoclusters.

* * * * *